United States Patent [19]

Miyazaki et al.

[11] Patent Number: 4,873,572
[45] Date of Patent: Oct. 10, 1989

[54] ELECTRONIC ENDOSCOPE APPARATUS

[75] Inventors: Akihiko Miyazaki; Tetsuo Nonami, both of Hachioji; Yuji Ikuno, Oume, all of Japan

[73] Assignee: Olympus Optical Co., Ltd., Tokyo, Japan

[21] Appl. No.: 160,051

[22] Filed: Feb. 24, 1988

[30] Foreign Application Priority Data

Feb. 27, 1987 [JP] Japan ................................. 62-44480
Mar. 31, 1987 [JP] Japan ................................. 62-79196

[51] Int. Cl.⁴ ........................... A61B 1/04; A61B 1/06
[52] U.S. Cl. ...................................... 358/98; 128/6; 358/88
[58] Field of Search ..................... 358/88, 98; 128/6

[56] References Cited

U.S. PATENT DOCUMENTS

| | | |
|---|---|---|
| 3,309,519 | 3/1967 | Euler et al. |
| 3,670,097 | 6/1972 | Jones |
| 4,359,757 | 11/1982 | Jaeger |
| 4,423,436 | 12/1983 | Kimura |
| 4,559,556 | 12/1985 | Wilkins |
| 4,615,332 | 10/1986 | Buess ........................ 128/6 |
| 4,651,201 | 3/1987 | Schoolman ................. 358/98 |

FOREIGN PATENT DOCUMENTS

3527653A1 12/1987 Fed. Rep. of Germany.
48-25360 7/1973 Japan.
61-80221 4/1986 Japan.

OTHER PUBLICATIONS

"Dreidimensionales Fernsehen", Gerhard Domanski, *Funkschau*, 25-26/1981, pp. 60-64.

Primary Examiner—Howard W. Britton
Attorney, Agent, or Firm—Armstrong, Nikaido, Marmelstein, Kubovcik & Murray

[57] ABSTRACT

This electronic endoscope apparatus comprises an elongate insertable part, two image forming optical systems provide in the tip part of the insertable part and an integrated imaging device provided in the tip part of the insertable part and having two imaging regions in which object images are formed by two image forming optical systems. The imaging device has, for example, one solid state imaging device having two imaging regions or has two solid state imaging devices made integral.

30 Claims, 14 Drawing Sheets

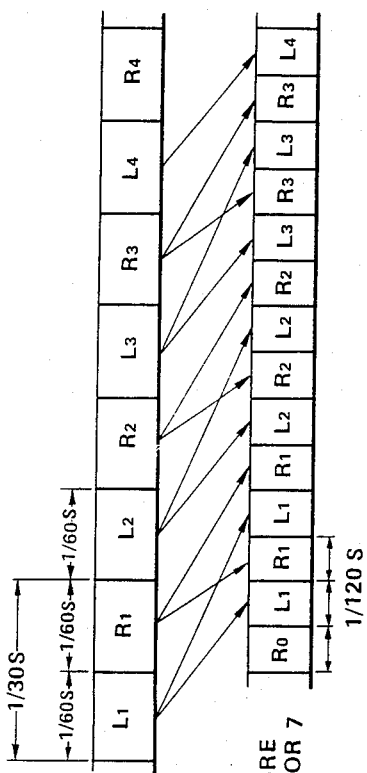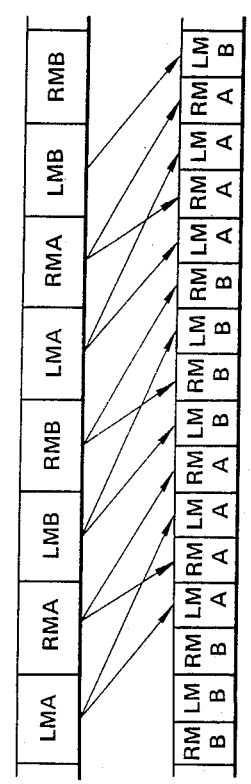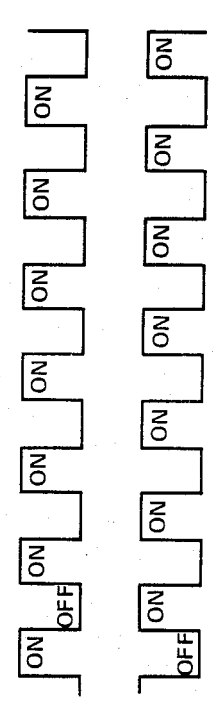
FIG.9(A) INPUT SIGNALS
FIG.9(B) DISPLAYED PICTURE IMAGES OF MONITOR 7
FIG.9(C) CONNECTION OF SWITCH 112
FIG.9(D) CONNECTION OF SWITCH 115
FIG.9(E) RIGHT EYE SHUTTER 123R
FIG.9(F) LEFT EYE SHUTTER 123L

ELECTRONIC ENDOSCOPE APPARATUS

BACKGROUND OF THE INVENTION

1. Field of the Invention

This invention relates to an electronic endoscope apparatus whereby a plurality of images can be formed and, for example, an imaged object can be three-dimensionally observed.

2. Related Art Statement

Recently, there is extensively utilized an endoscope whereby organs within a body cavity can be observed by inserting an elongated insertable part into the body cavity or, as required, various curing treatments can be made by using a treating tool inserted through a treating tool channel.

Also, there are suggested various electronic endoscopes wherein such solid state imaging device's as a charge coupled device (CCD) is used for the imaging means.

Now, as in finding an initial cancer, in some case, it is important to discriminate fine concavo-convexes on the surface. However, with the conventional endoscope, the observed or displayed image is plane and it has been difficult to discriminate fine concavo-convexes. Therefore, if the swelling state is so little as to be, for example, of the initial affected state, the affected state will be overlooked and it will be difficult to make a proper diagnosis.

Also, there are defects that, in the case of making a curing treatment by using a treating tool or the like, it will be difficult to positively catch the distance sense and the treatment will be a trouble.

By the way, an endoscope whereby a three-dimensional viewing is possible by using an image guide fiber bundle is mentioned in the gazette of a Japanese utility model publication No. 25360/1973. In this related art example, a pair of image guide fiber bundles for the right eye and left eye are required and there is a problem that the diameter becomes large over the entire length of the insertable part.

Also, in the gazette of a Japanese patent application laid open No. 80221/1986, there is disclosed a technique whereby a three-dimensional viewable image is obtained by a pair of image inverting prisms and a pair of electronic shutters and can be three-dimensionally viewed by spectacled switched and controlled as synchronized with the electronic shutter. However, in this related art example, the light path to the imaging device becomes so long that, if the optical system and imaging device are arranged in the tip part of the insertable part of the actual endoscope, the imaging part for obtaining a three-dimensional picture image will become too long. This imaging part can not be made bendable and therefore there is a defect that the rigid tip part becomes so long that a great pain will be forced to the patient in the case of inserting it.

There are also defects that, in case two independent solid state imaging devices are provided in the tip part of the insertable part, the outside diameter of the tip part will become large, will also force a great pair to the patient in the case of inserting it and the case of being able to use it will be restricted.

OBJECT AND SUMMARY OF THE INVENTION

An object of the present invention is to provide an electronic endoscope whereby a plurality of object images can be imaged without enlarging the diameter of the insertable part and the diameter and length of the rigid tip part of the insertable part.

Another object of the present invention is to provide an electronic endoscope apparatus whereby a three-dimensional observation is possible without enlarging the diameter of the insertable part and the diameter and length of the rigid tip part of the insertable part.

A further object of the present invention is to provide an electronic endoscope apparatus whereby a plurality of images can be obtained with one solid state imaging device and a three-dimensional observation is possible.

An electronic endoscope apparatus adapted to the three-dimensional observation of the present invention comprises an elongate insertable part, two image forming optical systems provided in the tip part of the above mentioned insertable part and an integrated imaging means provided in the tip part of the above mentioned insertable and having two imaging regions in which object images are formed by the above mentioned two image forming optical system. In one mode of the present invention, the above mentiond imaging means has a solid state imaging device having two imaging regions. In another mode of the present invention, the above mentioned imaging means has two integrated solid state imaging device. The above mentioned two image forming optical systems are arranged in two positions where the three-dimensional viewing is possible.

The other features and advantages of the present invention will become apparent enough with the following explanation.

BRIEF DESCRIPTION OF THE DRAWINGS

FIGS. 1 to 3 relate to the first embodiment of the present invention.

FIG. 1 is a block diagram showing the formation of an electronic endoscope apparatus.

FIG. 3 is a side view showing the entire electronic endoscope apparatus.

FIG. 5 is a block diagram showing the formation of an electronic endoscope apparatus.

FIG. 6(A) is a timing chart showing an input signal of a monitor.

FIG. 6(B) is a timing chart showing a displayed picture image of a monitor.

FIG. 6(C) is a timing chart showing the operation of a right eye shutter.

FIG. 6(D) is a timing chart showing the operation of a left eye shutter.

FIGS. 8 and 9 relate to the third embodiment of the present invention.

FIG. 8 is a block diagram showing the formation of an electronic endoscope apparatus.

FIG. 9(A) is a timing chart showing input signals of an A/D converter and synchronous separating circuit.

FIG. 9(B) is a timing chart showing displayed picture images of a monitor.

FIG. 9(C) is a timing chart showing the operation of a switch 112.

FIG. 9(D) is a timing chart showing the operation of a switch 115.

FIG. 9(E) is a timing chart showing the operation of a right eye shutter.

FIG. 9(F) is a timing chart showing the operation of the left eye shutter.

FIG. 10 is an explanatory view showing the tip part of the insertable part.

FIG. 11 is a block diagram showing the formation of an electronic endoscope apparatus.

FIG. 12 is an elevation of the tip part of the insertable part.

FIG. 13 is a perspective view showing two solid state imaging device and package.

FIG. 14 is an explanatory view showing a connector of the endoscope.

FIG. 18 is an explanatory view showing the tip part of the insertable part.

FIG. 19 is a block diagram showing a part of a video processor.

FIG. 20 is an explanatory view showing the tip part of the insertable part.

FIG. 21 is an arrangement explaining view of the tip part of the insertable part as seen from the front.

DETAILED DESCRIPTION OF THE PREFERRED EMBODIMENTS

Figure 1:
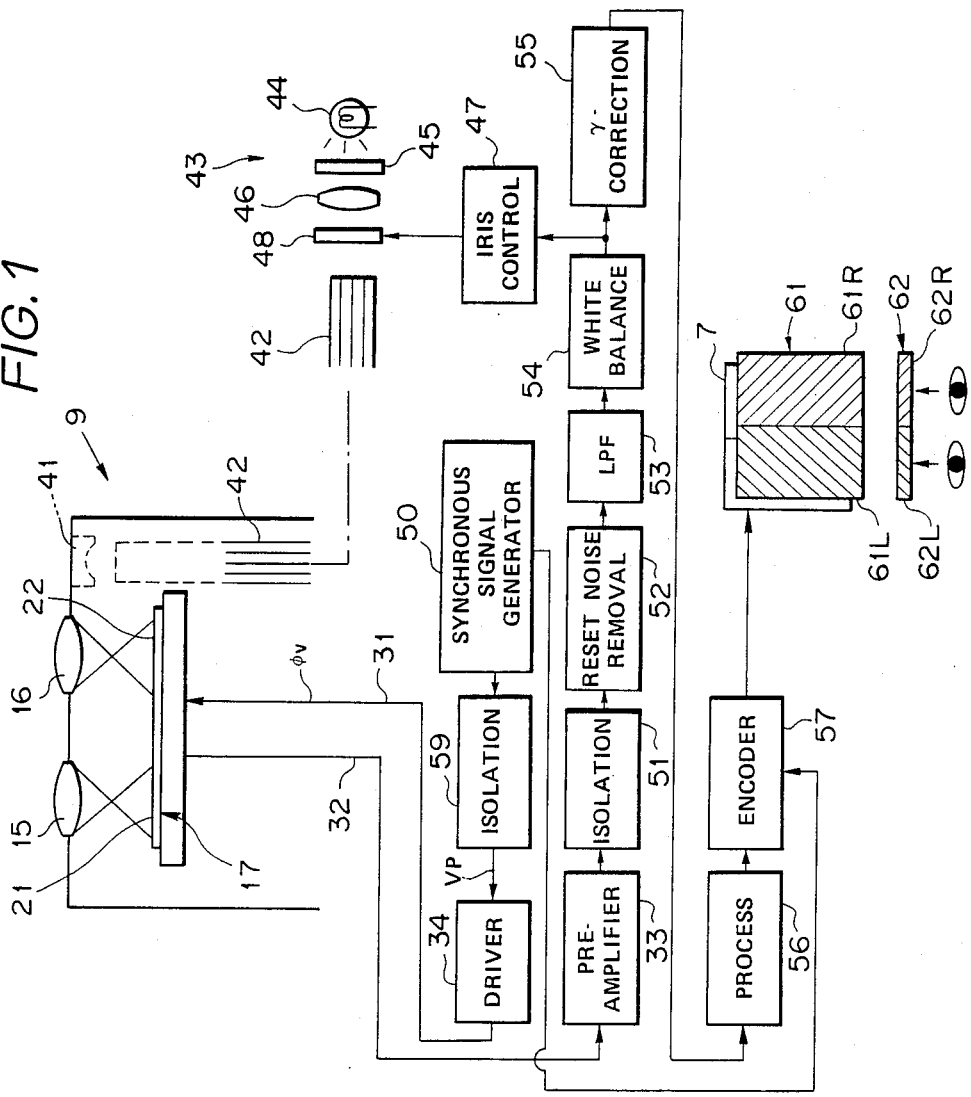
Figure 2A:
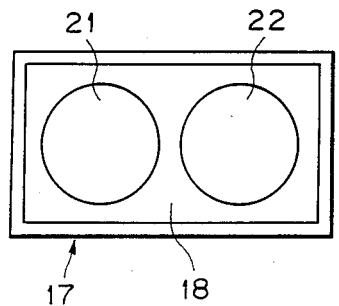
FIGS. 2(A) and 2(B) are explanatory views showing the image forming regions of a solid state imaging device.
Figure 2B:
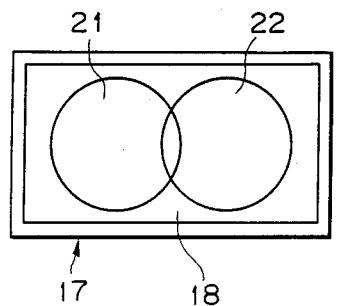
Figure 3:
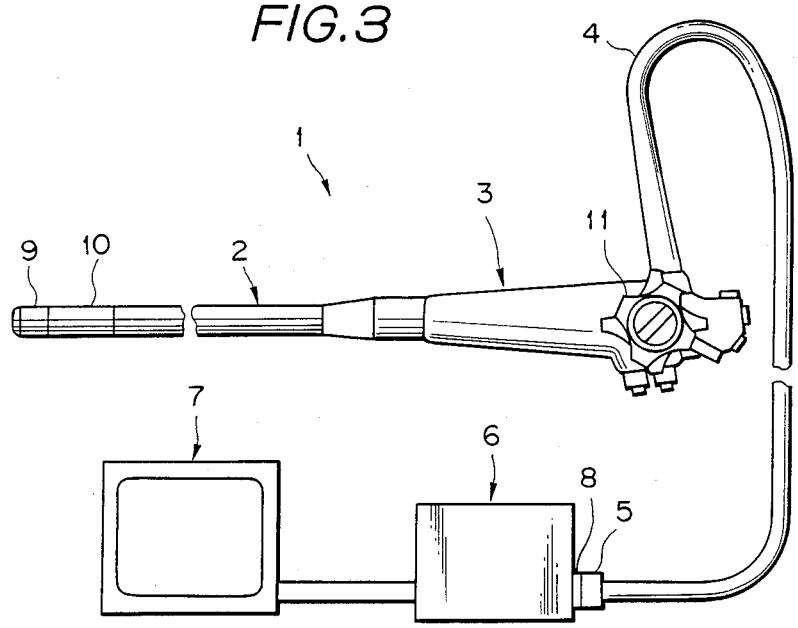

FIGS. 1 to 3 show the first embodiment of the present invention.

As shown in FIG. 3, an electronic endoscope 1 is provided with an elongate, for example, flexible insertable part 2 to the rear end of which a thick operating part 3 is connected. A flexible universal cord 4 is extended sidewise from the rear end part of the above mentioned operating part 3 and is provided with a connector 5 in the tip part. On the other hand, a control apparatus 6 containing a light source apparatus and signal processing circuit is provided with a connector receptacle 8 connectable with the above mentioned connector 5. The above mentioned electronic endoscope 1 is to be connected with the above mentioned control apparatus 6 by connecting the above mentioned connector 5 to the above mentioned connector receptacle 8. Further, a color monitor 7 as a displaying means is to be connected to the above mentioned control apparatus 6.

A rigid tip part 9 and a curvable part 10 adjacent to this tip part 9 and curvable to the rear side are provided in turn on the tip side of the above mentioned insertable part 2. The above mentioned curvable part 10 can be curved horizontally and vertically by rotating and operating the curving operation knob 11 provided in the above mentioned operating part 3.

In this embodiment, as shown in FIG. 1, a pair of objective lens systems 15 and 16 are arranged in parallel or as inclined inward in two positions where the tip side of the above mentioned tip part 9 can be three-dimensionally seen. One solid state imaging device 17 is arranged in the image forming positions of these objective lens systems 15 and 16. A filter array in which color filters transmitting respectively three primary colors, for example of red (R), green (G) and blue (B) are arranged in the form of a mosaic or the like is secured, though not illustrated, on the front surface of the imaging surface of this solid state imaging device 17.

As shown in FIGS. 1 and 2(A) and (B), the above mentioned solid state imaging device 17 has a long rectangular imaging surface 18 in the arranging direction of the above mentioned pair of the objective lens systems 15 and 16. Two image forming regions 21 and 22 in which object images are formed by the above mentioned pair of the objective lens systems 15 and 16 are provided on this imaging surface 18. These two image forming regions 21 and 22 may be provided without overlapping with each other as shown in FIG. 2(A) or as partly overlapped as shown in FIG. 2(B).

A driving pulse signal line 31 and signal output signal line 32 are connected to the above mentioned solid state imaging device 17, are inserted through the above mentioned insertable part 2 and universal cord 4 and are connected to the above mentioned connector 5. When the above mentioned connector 5 is connected to the connector receptacle 8 of the control apparatus 6, the above mentioned driving pulse signal line 31 will be connected to a driver 34 within the control apparatus 6 and the signal output signal line 32 will be connected to a pre-amplifier 33. By the way, this pre-amplifier 33 may be provided on the electronic endoscope 1 side.

A light distributing lens system 41 is arranged on the tip side of the above mentioned tip part 9. A light guide 42 formed of a flexible fiber bundle is provided in the rear of this light distributing lens system 41, is inserted through the above mentioned insertable part 2 and universal cord 4 and is connected to the above mentioned connector 5.

On the other hand, a light source apparatus 43 is provided within said control apparatus 6 and is provided with a lamp 44. The light emitted from this lamp 44 has infrared rays cut by an infrared ray cutting filter 45, is condensed by a condenser lens 46, further passes through a diaphragm 48 controlled by an iris controlling circuit 47 and enters the entrance end of the light guide 42 of the connector 5 connected to the connector receptacle 8 of the control apparatus 6. The illuminating light having entered this light guide 42 is led to the tip part 9 by this light guide 42, is emitted from the exist end and is radiated onto an object through the light distributing lens 41.

The reflected image of the object by this illuminating light passes through the objective lens systems 15 and 16 and is formed respectively in the image forming regions 21 and 22 of the solid state imaging device 17. The signal charge accumulated in this solid state imaging device 17 is transferred to a vertical transferring path if in an interline transferring system or to an accumulating part if in a frame transferring system according to the driving pulse $\Phi V$ output from the above mentioned driver 34 and is read out sequentially. The output signal read out of this solid state imaging device 17 is input into the above mentioned pre-amplifier 33 through the signal line 32. By the way, a vertical synchronous signal VP output from a synchronous signal generator 50 is input into the above mentioned driver 34 through an isolating process 59 isolating the part entering the patient body and the signal processing part from each other to protect the patient from electrification and the rise of the above mentioned driving pulse $\phi V$ and the above mentioned vertical synchronous signal VP are made to coincide with each other.

The output signal of the solid state imaging device 17 amplified by the above mentioned pre-amplifier 33 is processed as follows. That is to say, an isolating process 51 isolating the part entering the patient body and this signal processing part from each other in order to protect the patient from electrification and a reset noise removing process 52 for reducing the 1/f noise and reset noise generated mostly in the solid state imaging device 17 are made and then unnecessary components are removed by a low-pass filter 53. Further, the signal is adjusted in the white balance by the white balance adjusting circuit 54 and is then $\gamma$-corrected by a $\gamma$-correcting circuit 55. The electric signal-light converting characteristic of the cathode-ray tube is not linear but $\gamma=2.2$. This $\gamma$-correcting circuit 55 is to be provided to correct this non-linearity to be linear as a whole through the electronic endoscope 1 and the reciprocal number $\gamma=0.45$ of $\gamma=2.2$ is general. The output of this $\gamma$-correcting circuit 55 is input into the process circuit 56. For example, a luminance signal and color difference signals are produced by this process circuit 56. Further, a video signal, for example, of the NTSC system is produced by an encoder 57 from the output of the above mentioned process circuit 56 and is input into the color monitor 7 to color-display the object.

By the way, the above mentioned synchronous signal generator 50 applies a synchronous signal to the above mentioned encoder 57 to process the signal to be synchronized with the driving pulse $\Phi V$ used to read out the signal of the solid state imaging device 17.

The output of the above mentioned white balance adjusting circuit 54 is input also into the iris controlling circuit 47 to control the diaphram 48 by the size of the voltage level integrating the output signal of the above mentioned white balance adjusting circuit 54.

The object image of the visual field of the objective lens system 15 formed in the image forming region 21 and the object image of the visual field of the objective lens system 16 formed in the image forming region 22 in the solid state imaging device 17 are simultaneously displayed on the right and left and are somewhat displaced from each other by the parallax between both eyes.

In this embodiment, a polarizing plate 61 passing only the lights in the polarizing directions different from each other in the left side part 61L and right side part 65R is fitted to the front surface of the above mentioned color monitor 7. By observing the video image of this color monitor 37 through polarizing spectacles 62 having the left part 62L passing only the light in the same polarizing direction as of the left side part 61L of the above mentioned polarizing plate 61 corresponding to the left eye and a right part 62R passing only the light in the same polarizing direction as of the right side part 61R of the above mentioned polarizing plate, the object image of the visual field of the objective lens system 15 will be observed by the left eye and the object image of the visual field of the objective lens system 16 will be observed by the right eye. Therefore, by the difference of the visual fields of both objective lens systems 15 and 16, a three-dimensional image of the object will be observed.

In this embodiment formed as in the above, the object images of the visual fields of a pair of objective lens systems 15 and 16 arranged in two positions where a three-dimensional viewing is possible are formed respectively in the two image forming regions 21 and 22 on the imaging surface 18 of one solid state imaging device 17. The output signal of this solid state imaging device 17 is processed to be a video signal by a signal processing circuit within the control apparatus 6 and the video signal is input into the color monitor 7. The object image of the visual field of the objective lens system 15 formed in the image forming region 21 and the object image of the visual field of the objective lens system 16 formed in the image forming region 22 in the above mentioned solid state imaging device 17 are simultaneously displayed on the right and left. By observing the video image of this color monitor 7 through the polarizing plate 61 and polarizing spectacles 62, a three-dimensional or stereo-image of the object can be observed.

Thus, according to this embodiment, as a three-dimensional or stereo-image of an object can be observed, minute concavo-convexes on the object surface can be discriminated and an initial cancer or the like can be easily found.

Also, according to this embodiment, it is not necessary to insert a pair of image guides through the insertable part 2 and therefore the diameter of the insertable part 2 does not become large.

Further, the object images of the visual fields of the pair of the objective lens systems 15 and 16 formed simultaneously on the imaging surface 18 of one solid state imaging device 17 are simultaneously imaged and displayed in a color monitor 7 at a real time.

As the object images of the visual fields of the pair of the objective lens systems 15 and 16 can be imaged, as compared with the case of providing two independent solid state imaging devices, the formation is simpler and the diameter of the tip part 9 can be reduced.

By the way, in this embodiment, in the course of the signal processing circuit, for example, after the encoder 57, a visual field converting apparatus is provided so that the visual field may be converted and a better three-dimensional or stereo-sense may be obtained.

Figure 4:
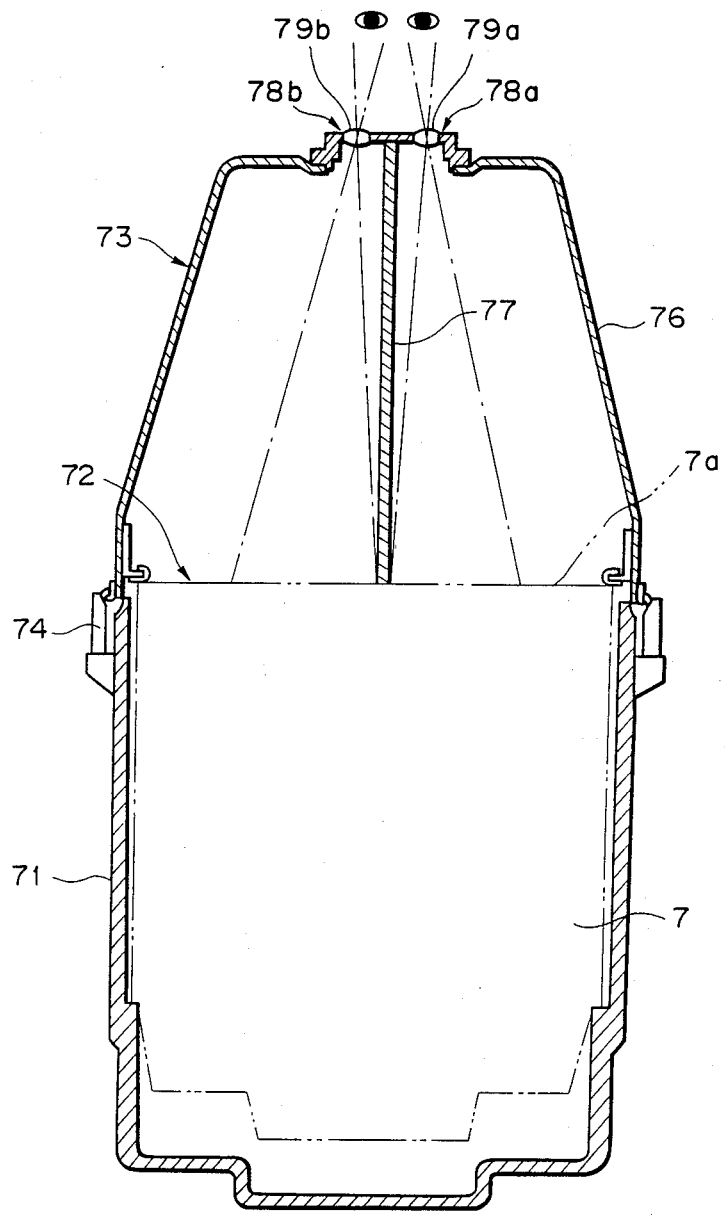
FIG. 4 is an explanatory view showing a displaying apparatus relating to a modification of the first embodiment.

FIG. 4 is an explanatory view showing a displaying apparatus related to a modification of the first embodiment.

In this modification, the color monitor 7 is contained within a housing 71 having an opening 72 on the displaying surface 7a side. An adapter member 73 is fitted removably to the opening 72 of this housing 71 by an engaging means 74. This adapter member 73 is provided with a hood part 76 covering the displaying surface 7a side of the above mentioned color monitor 7 and a partition plate 77 dividing the interior of this hood part 76 into the right and left of the displaying surface 7a of the above mentioned color monitor 7. In the above mentioned hood part 76, observing windows 78a and 78b are provided at a spacing corresponding to both right and left eyes on the right and left by holding the above mentioned partition plate 77 in the part opposed to the displaying surface 7a of the above mentioned color monitor 7 and are fitted respectively with lenses 79a and 79b. When the displaying surface 7a of the above mentioned color monitor 7 is observed through the above mentioned lenses 79a and 79b with both right and left eyes, the left eye will be able to observe only the left side part of the above mentioned displaying surface 7a and the right eye will be able to observe only the right side part of the above mentioned displaying surface 7a.

In the above mentioned color monitor 7, the same as in the first embodiment, the object image of the visual field of the objective lens system 15 formed in the image forming region 21 and the object image of the visual field of the objective lens system 16 formed in the image forming region 22 in the solid state imaging device 17 are displayed simultaneously on the right and left. Therefore, when the video image of this color monitor 7 is observed from the observing windows 78a and 78b of the above mentioned adapter member 73, a three-dimensional or stereo-image of the object will be able to be observed.

Figure 5:
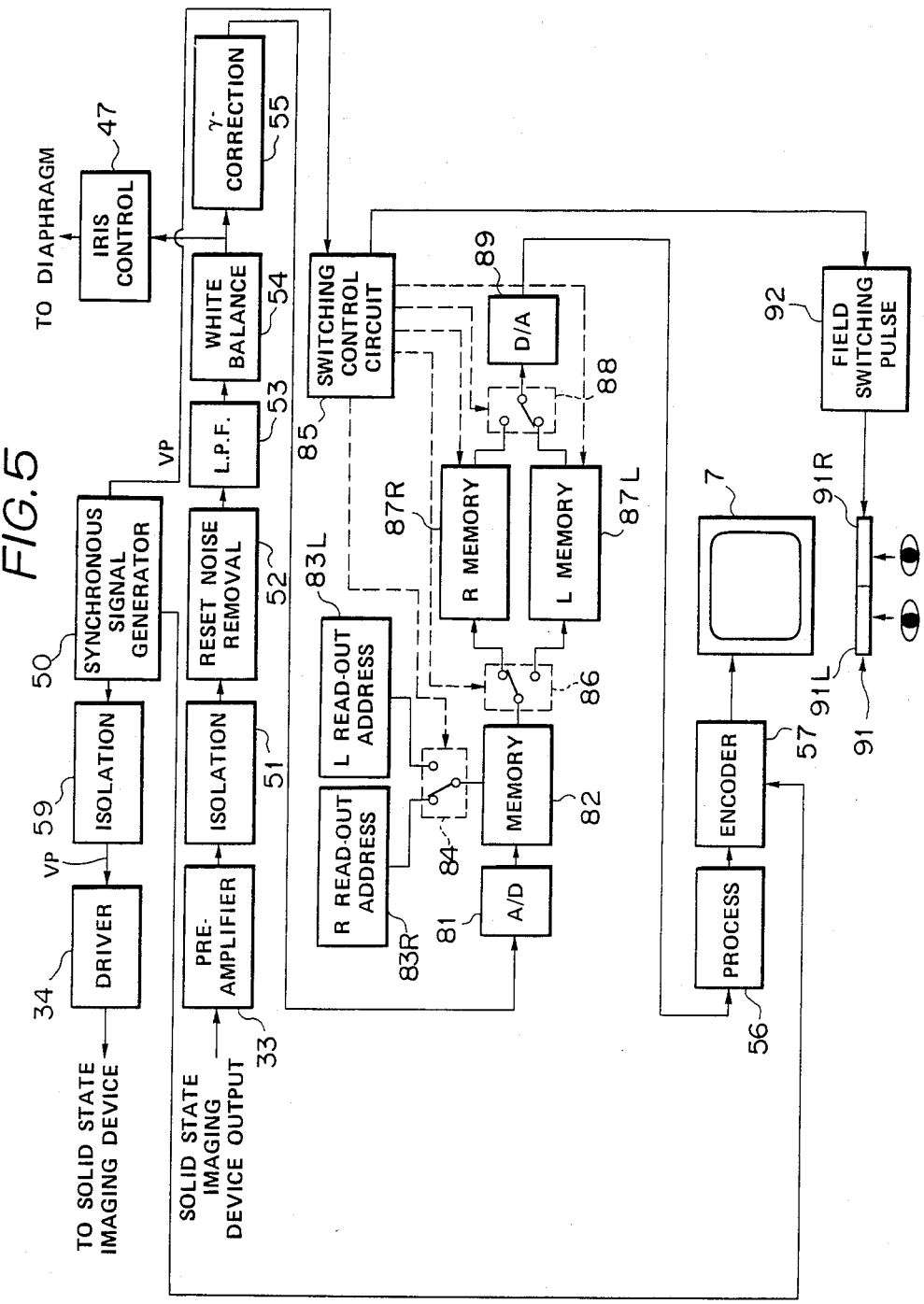
FIGS. 5 and 6 relate to the second embodiment of the present invention.
Figure 6:
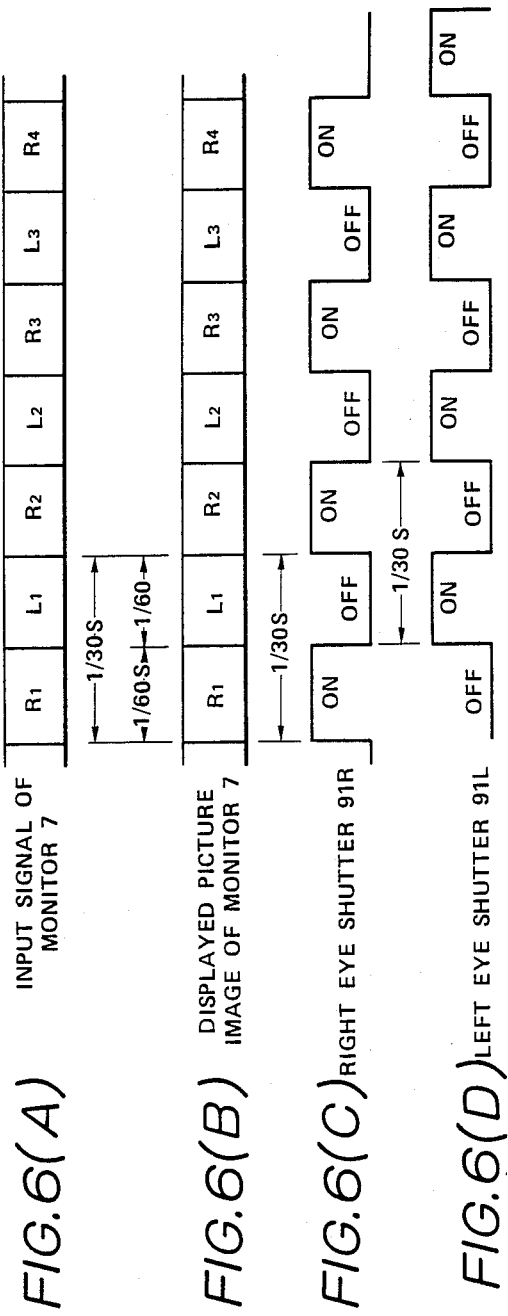

FIGS. 5 and 6 show the second embodiment of the present invention.

In this embodiment, the output signal of the γ-correcting circuit 55 is converted to a digital signal by an A/D converter 81 and is memorized in a memory 82. In this memory 82, two read-out addresses can be designated by tow read-out address generators 83L and 83% switched and connected through a switching switch 84. One read-out address generator 83L generates an address reading out the left half of a picture image memorized in the above mentioned memory 82, that is, the object image of the visual field of the objective lens system 15 formed in the image forming region 21 of the solid state imaging device 17. The other read-out address generator 83R generates an address reading out the right half of a picture image memorized in the above mentioned memory 82, that is, the object image of the visual field of the objective lens system 16 formed in the image forming region 22 of the solid state imaging device 17.

In this embodiment, in the above mentioned solid state imaging device 17, in each field, the object image of the visual field of the objective lens system 15 and the object image of the visual field of the objective lens system 16 are simultaneously imaged. Both of these object images are memorized in the above mentioned memory 82. The above mentioned switching switch 84 is switched for each field by the switching controlling signal produced by a switching controlling circuit 85 on the basis of a vertical synchronous signal VP from a synchronous signal generator 50. Therefore, in the above mentioned memory 82, the left half of the memorized picture image, that is, the object image of the visual field of the objective lens system 15 formed in the image forming region 21 of the solid state imaging device 17 and the right half of the memorized picture image, that is, the object image of the visual field of the objective lens system 16 formed in the image forming region 22 of the solid state imaging device 17 are alternately read out in each field.

The signal read out of the above mentioned memory 82 is memorized alternately in the memory 87L and memory 87R through a switching switch 86. Further, the above mentioned memories 87L and 87R are controlled by the above mentioned switching controlling circuit 85, the signal written in is read out alternately in each field, is input into a D/A converter 89 through a switching switch 88 switches as synchronized with the above mentioned switching switches 84 and 86 by the switching controlling signal produced by the above mentioned switching controlling circuit 85, is converted to an analogue signal by this D/A converter 89 and is input into the process circuit 56 and, for example, a luminance signal and color difference signals are produced by this process circuit 56. Further, a video signal, for example, of an NTSC system is produced by the encoder 57 from the output of the above mentioned process circuit 56, is input into the color monitor 7 to color-display the object.

In the above mentioned color monitor 7, as shown in FIG. 6 (A), in each field (1/60 second), the video signal of the image memorized in the memory 87R and the video signal of the image memorized in the memory 87L are input alternately and therefore, in this color monitor 7, as shown in FIG. 6 (B), the object image of the visual field of the objective lens system 16 and the object image of the visual field of the objective lens system 15 are displayed alternately in each field. By the way, the period of the display of one image is 1/30 second. In FIG. 6, the symbol R represents the object image of the visual field of the objective lens system 16, L represents the object image of the visual field of the objective lens system 15 and the attached numeral represents the frame number.

In this embodiment, by observing the video image of the above mentioned color monitor 7 through a shutter 91, a three-dimensional or stereo-image of the object can be observed. The above mentioned shutter 91 is formed of a right eye shutter 91R corresponding to the right eye and a left eye shutter 91L corresponding to the left eye. Both shutters 91R and 91L alternately intercept the light in each field as shown in FIGS. 6 (C) and (D) by a switching controlling circuit 85. By observing the video image of the above mentioned color monitor through this shutter 91, for example, the object image of the visual field of the objective lens system 15 is observed with the left eye and the object image of the visual field of the objective lens system 16 is observed with the right eye. Therefore, a three-dimensional or stereo-image of the object is observed by the difference between the visual fields of both objective lens systems 15 and 16. By the way, one eye observes the video image for 1/60 second every 1/30 second. By the way, in FIG. 6, the open state of the shutter 91R and 91L is represented by ON and the closed state is represented by OFF.

The above mentioned shutter 91 may be an electronic optical shutter formed, for example, of a PLZT or liquid crystal.

The other formations are the same as in the first embodiment.

According to this embodiment, the image corresponding to the right eye and the image corresponding to the left eye can be separated from each other. The respective images can be independently recorded and stopped.

By the way, in this embodiment, the D/A converter, process circuit and encoder may be provided respectively in the rear steps of the memorys 87R and 87L and the right and left images may be displayed in respectively separate monitors. The video images of the respective monitors may be observed with the right and left eyes by using such means as the polarizing plate, polarizing spectacles and adapter member shown in the first embodiment.

The other operations and effects are the same as in the first embodiment.

In this embodiment, too, in the course of the signal processing circuit or, for example, after the encoder 57, a visual field converting apparatus may be provided to convert the visual field and to obtain a better stereo-sense.

Figure 7:
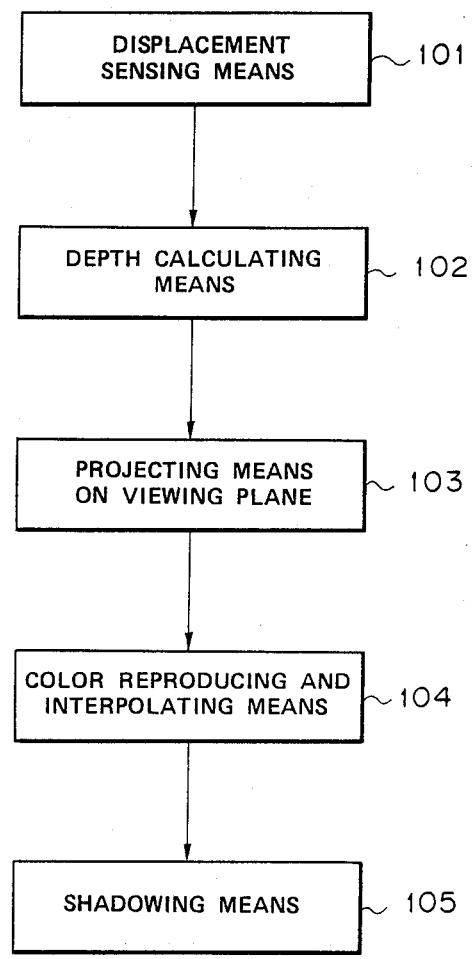
FIG. 7 is a flow chart showing the operation of a visual field converting apparatus.

The above mentioned visual field converting apparatus is processed, for example, as shown in FIG. 7.

First, the geometric strain of the lens is corrected and then the difference (displacement) of the view of an object between two picture images obtained by a displacement detecting means 101 is sensed by such means as a correlation. Then, the distance (depth) from the front surface of the endoscope to each point of the object is geometrically calculated by a depth calculating means 102 to prepare a three-dimensional information of the object. Then, by a projecting means 103 on the viewing plane, a proper viewing point is determined for the three-dimensional information of the object determined by the above mentioned depth calculating means 102 and a viewing coordinates projected on the viewing plane of each of the right eye and left eye are calculated. Then, by a color reproducing and interpolating means 104, a color information projected on the viewing plane is determined from the original picture image. The clearances of the respective points are interpolated. (At this time, a surface hiding process hiding surfaces not seen is made.) Finally, the respective points are shadowed by a shadowing means 105.

Even if two original picture images are merely three-dimensionally or stereo-viewed, the distance between both eyes will be small. Also, the lens of the endoscope is generally of a wide angle. Therefore, a sufficient stereo-sense is hard to obtain. Therefore, by converting the parallax by using the above mentioned visual field converting apparatus, a favorable stereo-sense can be obtained with the ordinary human eye.

Figure 8:
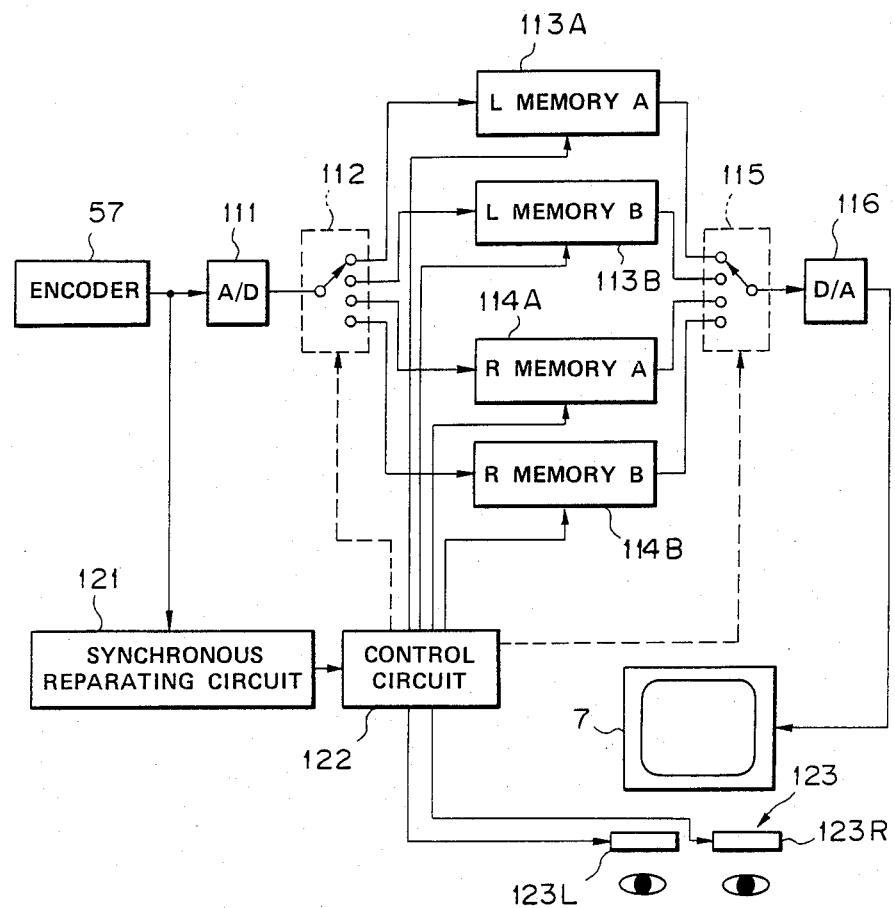

FIGS. 8 and 9 show the third embodiment of the present invention.

In this embodiment, the video signal output of the encoder 57 in the second embodiment shown, for example, in FIG. 5 is input into an A/D converter 111 as shown in FIG. 8 and is converted to a digital signal. This A/D converter 111 is connected to the fixed contact of a 4-contact switching switch 112 formed of a semiconductor switch or the like. The respective switching contacts of this switching switch 112 are connected to the data input ends of two sets of memories, that is, a left picture image (L) memory A113A, left picture image (9L) memory B 113B and right picture image (R) memory A114A, right picture image (R) memory B114B. The output of the above mentioned A/D converter 111 is selectively memorized in these memories 113A, 113B, 114A and 114B through the above mentioned switching switch 112. The above mentioned memories 113A, 113B, 114A and 114B may be such dual port memories as, for example, M5M4C500L made by Mitsubishi Electric Co.

The respective data output ports of the above mentioned memories 113A, 113B, 114A and 114B are connected to the respective switching contacts of a 4-contact switching switch 115 formed of a semiconductor switch or the like. The fixed contact of this switching switch 115 is connected to a D/A converter 116. The read-out outputs of the above mentioned memories 113A, 113B, 114A and 114B selectively output through the above mentioned switching switch 115 are converted to analogue signals by the above mentioned D/A converter 116 and are input as video signals into the color monitor 7.

The output of the above mentioned encoder 57 is input also into a synchronous separating circuit 121 and only a synchronous signal is taken out of this synchronous separating circuit 121. The synchronous signal taken out of this synchronous separating circuit 121 is input into a control circuit 122 generating various controlling timing signals. The above mentioned switching switches 112 and 115 and memories 113A, 113B, 114A and 114B are controlled as shown in FIG. 9 by a timing signal from the above mentioned control circuit 122.

That is to say, as shown in FIG. 9 (A), the right eye picture images (R1, R2, ...) and left eye picture images (L1, L2, ...) are alternately input in each field, that is, every 1/60 second, into the A/D converter 111 and synchronous separating circuit 121. As shown in FIG. 9 (C), the above mentioned switching switch 112 is switched in each field as synchronized with the above mentioned input signal. The left eye picture images L1, L3, ... of odd number frames are memorized in the left picture image memory A113A, the right eye picture images R1, R3, ... of odd number frames are memorized in the right picture image memory A114A, the left eye picture images L2, L4, ... of even number frames are memorized in the left picture image memory B113B and the right picture images R2, R4, ... of even number frames are memorized in the right picture image memory B114B.

On the other hand, as shown in FIG. 9 (D), the above mentioned switching switch 115 is switched every ½ the period of the above mentioned switching switch 112, that is, every 1/120 second. In the period while the picture images are being memorized in the left picture image memory A113A, the picture images will be read out of the right picture image memory B114B and the other left picture image memory B114 respectively in the period of 1/120 second. In the period while the picture images are being memorized in the right picture image memory A114A, the picture images will be read out of the other right picture image memory B114B and the left picture image memory A113A respectively in the period of 1/120 second. In the period while the picture images are being memorized in the left picture image memory B113B, the picture images will be read out of the right picture image memory A114A and the other left picture image memory A113A in the period of 1/120 second. In the period while the picture images are being memorized in the right picture image memory B114B, the picture images will be read out of the right picture image memory A114A and the left picture memory B113B in the period of 1/120 second.

The read-out outputs of the above mentioned respective memories 113A, 113B, 114A and 114B are converted to analogue signals by the above mentioned D/A converter 116 and are input as video signals into the color monitor 7. Therefore, in this color monitor 7, as when in FIG. 9 (B), the right eye picture images (R0, R1, ...) and left eye picture images (L1, L2, ...) are alternately displayed in each ½ field, that is, every 1/120 second. By the way, the picture images are read twice out of the respective memories 113A, 113B, 114A, 114B and are therefore displayed twice.

In this embodiment, by observing the video images of the above mentioned color monitor 7 through the same shutter 123 as the shutter 91 in the second embodiment, the stereo-image of the object can be observed. The above mentioned shutter 123 is formed of a right eye shutter 123R corresponding to the right eye and a left eye shutter 123L corresponding to the left eye.

As synchronized with the switching of the displayed picture image of the color monitor 7 so that, by the switching controlling signal from the above mentioned controlling circuit 122, as shown in FIGS. 9 (E) and (F), when the right eye picture image is displayed in the color monitor 7, only the right eye shutter 123R will be open and, when the left eye picture image is displayed, only the left eye shutter 123L will be open, one of these shutter 123R and 123L alternately intercepts the light in each ½ field, that is, every 1/120 second. When the video image of the above mentioned color monitor 7 is observed through this this shutter 123, the right eye picture image will be observed with the right eye, the left eye picture image will be observed with the left eye and a stereo-image of the object will be observed. By the way, one eye will observe the video-image for 1/120 second every 1/601 second. By the way, in FIG. 9, the opened state of the shutters 123R and 123L is represented by ON and the closed state is represented by OFF.

The same as in the second embodiment, the above mentioned shutter 123 may be such electronic optical shutter formed, for example, of a PLZT or liquid crystal. Also, the above mentioned shutter 123 may be controlled with a wireless or infrared rays.

The other formations are the same as in the second embodiment.

In the second embodiment, as one eye observes the video image for 1/60 second every 1/30 second, the residual image effect of the human eye may not operate and the observer may feel a flicker. On the other hand, according to this embodiment, the right eye picture image and the left eye picture image are switched over to each other at a speed twice as high as in the second embodiment, one eye observes the video image for 1/120 second every 1/60 second and therefore, by the residual image effect of the human eye, no flicker will be felt.

By the way, the speed of switching the right eye picture image and left eye picture image is not limited to the speed twice as high as in the second embodiment but may be set freely.

By the way, the part from the A/D converter 111 to the D/A converter 116 shown in FIG. 8 may be provided, for example between the D/A converter 891 and the process circuit 56 in FIG. 5 instead of being provided in the rear step of the encoder 57.

The other operations and effects are the same as in the second embodiment.

By the way, in the first to third embodiments, a plurality of image forming optical systems may be formed by moving the objective lens system.

Thus, according to the first to third embodiments, there are effects that a plurality of object images can be imaged with one solid state imaging device, a plurality of picture images having parallaxes can be obtained without enlarging the diameter and length of the rigid tip part of the insertable part and, for example, an object can be stereo-observed or three-dimensionally.

FIGS. 10 to 14 show the fourth embodiment of the present invention.

Figure 11:
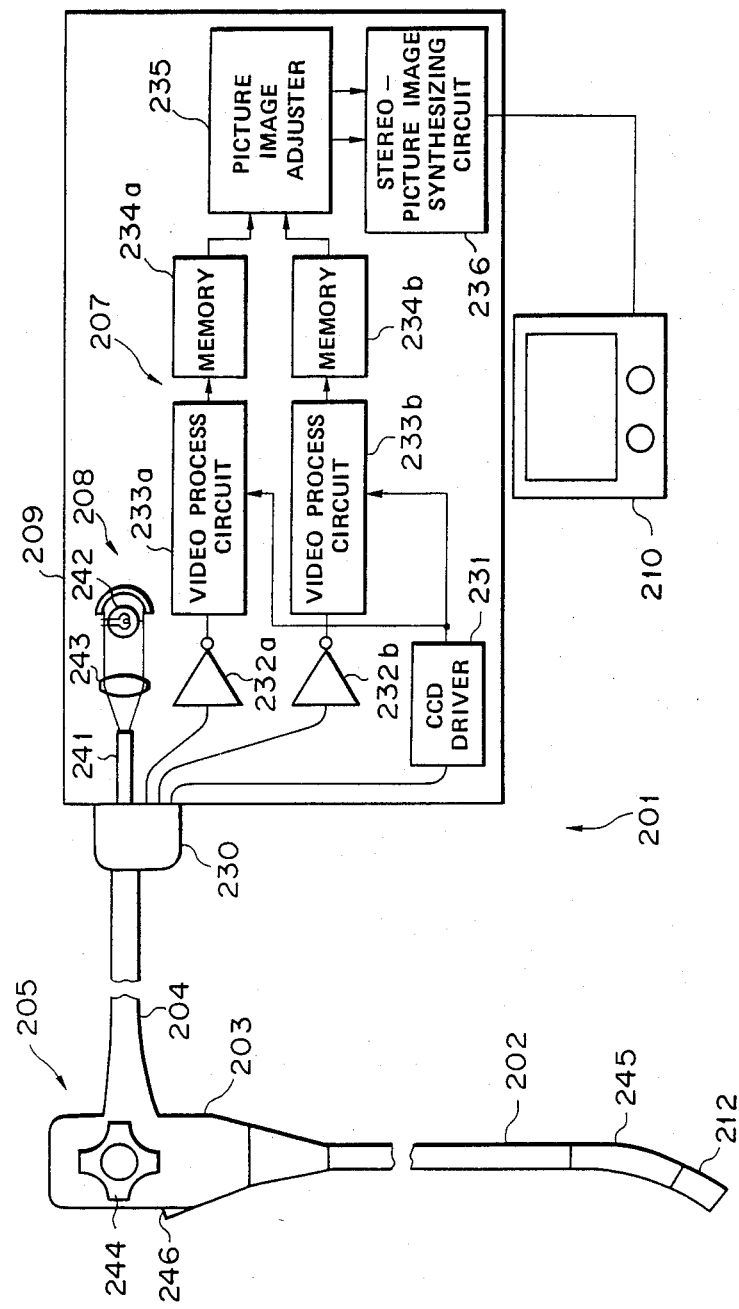

As shown in FIG. 11, a stereo-viewing electronic endoscope apparatus 201 of the fourth embodiment comprises an electronic endoscope 205 provided with an elongate insertable part 202, an operating part 203 connected to the rear end of this insertable part 202 and a universal cord 204 extended out of this operating part, a video processor 209 having this electronic endoscope 205 removably connected to and containing a video signal processing part 207 and a light source part and a color monitor 210 displaying a picture image imaged by a video signal video-processed by this video processor 209.

Figure 10:
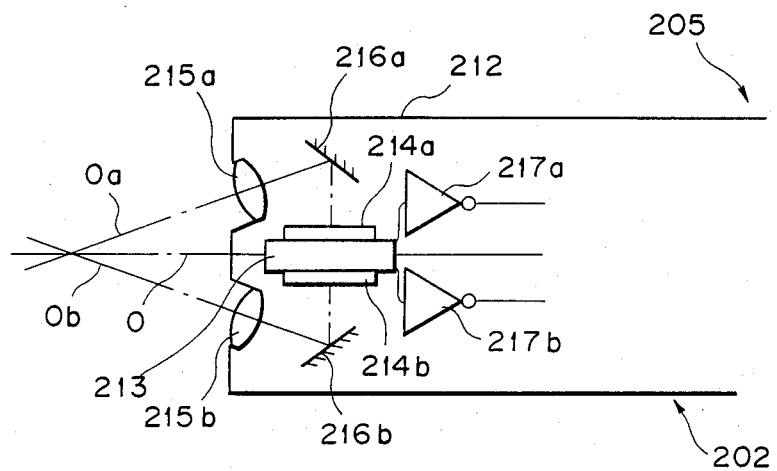
FIGS. 10 to 14 relate to the fourth embodiment of the present invention.

A stereo-viewing imaging means is incorporated as shown in FIG. 10 in the tip part 212 of the insertable part 202 of the above mentioned electronic endoscope 205.

That is to say, a plate-like package 213 is arranged by having its center coinciding with the center axis 0 of the tip part 212 cylindrical in the contour. Two CCD 214a and 214b as solid state imaging devices are fitted on both surfaces of this package 213.

Two objective lenses 215a and 215b are symmetrically arranged on both sides of the plate surface of the package 213 arranged along the above mentioned center axis 0. Mirrors 216a and 216b are symmetrically arranged in the rear positions (with respect to the incident light) on the optical axes 0a and 0b of the respective objective lenses. A stereo-viewing imaging means is formed of these two imaging means, that is, objective lenses 215a, 215b; mirrors 216a, 216b; CCD 214a, 214b. That is to say, the light from an object in the front position of the optical axis 0a (or 0b) of the objective lens 215a (or 215b) passes through the objective lens 215a (or 215b), is reflected by the mirror 216a (or 216b) in the rear of this optical axis 0a (or 0b), is made to form an image on the imaging surface of the CCD 214a (or 214b) and is photoelectrically converted to be a video signal. The respective video signals read out of the respective CCD 214a and 214b are transmitted to the video processor 209 side through buffers 217a and 217b contained within the tip part 212.

By the way, the above mentioned two optical axes 0a and 0b intersect each other on the center axis 0. This intersecting angle is set to be in a range, for example, of 10 to 12 degrees. This angle is set to be of a value different in response to the object to be observed.

Figure 12:
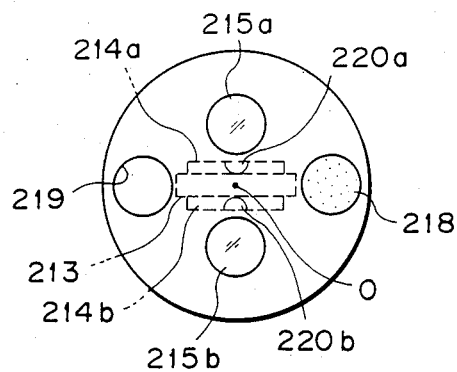

The above mentioned two stereo-viewing imaging means arranged symmetrically with respect to the center axis 0 as seen from the front of the tip part 212 are as shown in FIG. 12. The objective lenses 215a and 215b are arranged on both sides (on both sides in the vertical direction in this case) of the plate surface of the package 213 arranged along the center axis 0 and a light guide 218 and a forceps port 219 are arranged on both sides, in the horizontal direction of this center axis 0. Nozzle parts 220a and 220b in the tip of an air and water feeding type inserted through the insertable part 2 are formed to be directed to the objective lenses 215a and 215b near the tip part 212.

Figure 13:
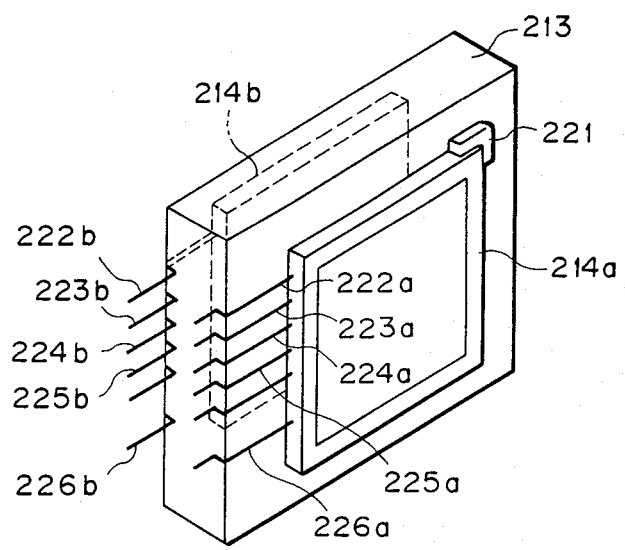

The above mentioned two CCD 214a and 214b are preferably of the same number of pixels and the uniform characteristic. As shown in FIG. 13, these CCD 214a and 214b are fixed to both surfaces of the package 213 with a bonding agent. In this case, in fitting the two CCD 214a and 214b, the two imaging surfaces are positioned with each other, for example, by L-like positioning parts 221 (only one is shown in the drawing) provided on the respective surfaces of the package 213. Power source leads 222a and 222b, horizontal driving signal driving leads 223a and 223b, vertical driving signal driving leads 224a and 224b, antiblooming gate driving leads 225a and 225b and CCD output leads 226a and 226b are respectively formed from the CCD 214a and 214b fitted to this package 213. Both CCD 214a and 214b are fitted so that the respective leads can be pulled out in the same direction.

As shown in FIG. 11 a driving signal is applied through a CCD driver 231 to the above mentioned respective CCD 214a and 214b to output video signals. By the way, this driving signal is used in common by both CCD 214a and 214b. Therefore, the frequencies of the driving signal are naturally equal. The video signals read out of the respective CCD 214a and 214b pass through the buffers 217a and 217b and are amplified respectively by the pre-amplifiers 232a and 232b within the video processor 209 to which is connected a connector 230 formed at the end of the universal cord 204. The respective amplified signals are input respectively into video process circuits 233a and 233b and are processed to be such television signals as a luminance signal Y and color difference signals R-Y and B-Y or to be converted to color signals R, G and B. The signals processed by the video process circuits 233a and 233b are memorized respectively in memories 234a and 234b.

The signals memorized in the above mentioned memories 234a and 234b are input into a picture image adjuster 235 and are corrected in the sizes and positions of the picture images of the two CCD 214a and 214b by the picture image adjuster 235 and are then input into a stereo-picture image synthesizing circuit 236. By this stereo-picture image synthesizing circuit 236, the signal data of the above mentioned memories 234a and 234b are operated to produce a three-dimensional picture image signal which is fed to the color monitor 210 to display a stereo-picture image on its displaying picture surface.

By the way, the above mentioned picture image adjuster 235 is known to detect and correct the difference from the comparison of the memory addresses of specific picture images contained in the memories 234a and 234b and the frequency components included in 1 scanning time.

Now, by connecting the connector 230 of the above mentioned universal cord 204, the white light of the light source lamp 242 is condensed by a lens 243 and is radiated onto a light guide connector.

By the way, the operating part 204 of the above mentioned electronic endoscope 205 is provided with a curving operation knob 244. By rotating this knob 244, the curvable part 245 formed to be adjacent to the tip part 212 can be bent.

Within the insertable part 202, a forceps channel not illustrated is formed. The operating part 204 is provided with a forceps introducing part 246. The forceps is inserted into this introducing part 246, is passed through the above mentioned forceps channel and can be projected on the tip side out of a forceps part 219 of the tip part 212.

Figure 14:
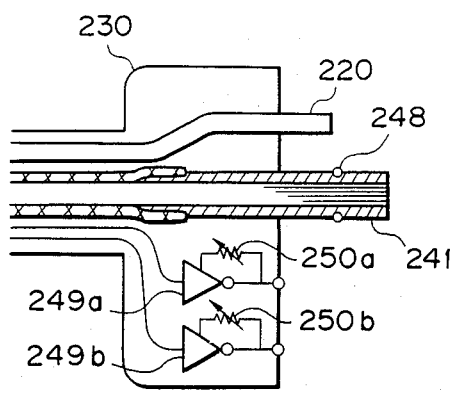

By the way, in the connector 230 of the universal cord 204, as shown in FIG. 14, a C-ring 248 is contained within a peripheral groove formed on the outer periphery of a mouthpiece of the light guide connector 241. By inserting the light guide connector 241 fitted with this C-ring 248 into a (light guide) connector receptacle part, there is formed a cooperating means holding the connected state so that the C-ring 248 may be prevented by the connector receptacle side clicking mechanism from being accidentally pulled out.

Also, as shown in FIG. 14, signal level adjusters 249a and 249b for regulating the signal levels of the output signals of the CCD 214a and 214b having passed through the buffers 217a and 217b are contained within the above mentioned connector 230. By these signal level adjusters 249a and 249b, even if there is any dispersion between the CCD 214a and 214b, by adjusting the values of gain adjusting resistances 250a and 250b, the gain can be varied and can be set at an equal output level. Also, by these signal level adjusters 249a and 249b, even the output level of a different electronic endoscope can be arranged. Thus, it is not necessary to adjust the signal level on the video processor 209 side for each connected electronic endoscope.

By the way, the above mentioned signal level adjusters 249a and 249b are not limited to be provided within the connector 230 but may be provided, for example, within the operating part 20.

Also, the above mentioned connector 230 is provided with an air and water feeding pipe 220 so as to be connected with an air and water feeding means not illustrated on the video processor 209 side.

According to the thus formed fourth embodiment, two CCD 214a and 214b are pasted on both surfaces of one sheet of the package 213 so as to be integral. It is a feature that the package 213 fitted with these CCD 214a and 214b is arranged in the center part of the tip part 212 so that the images of an object may be formed on the respective imaging surfaces of these CCD 214a and 214b by using the objective lenses 215a and 215b and mirrors 216a and 216b.

According to the thus arranged fourth embodiment, as shown in FIG. 10, a stereo-viewing imaging means can be arranged within a compact and shall space and therefore can be contained within the tip part 212 small in the outside diameter and short in the length.

Therefore, the pain given to the patient in inserting it can be made small and the diameter can be made small. Therefore, uses as inserted are not restricted and are extensive.

Figure 15:
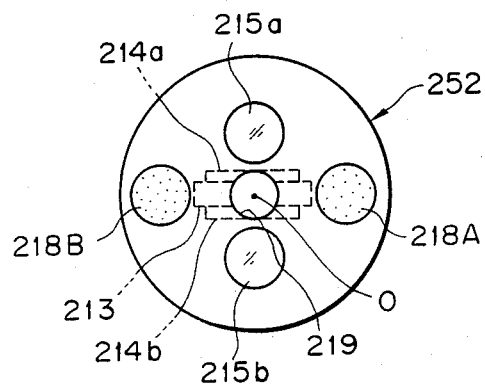
FIG. 15 is an elevation of the tip part of the insertable part in the fifth embodiment of the present invention.

FIG. 15 shows the fifth embodiment of the present invention.

This fifth embodiment is that, in the above mentioned fourth embodiment, the light guide 218 inserted through the insertable part 202 is branched into two parts near the tip of the insertable part 202 and the two branched tip surfaces 218A and 218B are arranged symmetrically in the horizontal direction with respect to the center axis 0. That is to say, so that the segment connecting the two objective lenses 215a and 215b arranged symmetrically in the vertical direction with respect to the center axis 0 and the segment connecting the two light guide tip surfaces 218A and 218B may intersect at right angles with each other at the center axis 0.

By thus arranging them, the light distribution balance and brightness of the illuminating light for the lights forming the respective optical images entering the objective lenses 215a and 215b can be improved and a desirable stereo-picture image can be obtained.

By the way, in this fifth embodiment, the forceps part 219 is located on the center axis 0 (the tip part is located at the center axis 0 by detouring to avoid the package 213 part near the tip of the insertable part 202). The others are the same as in the above mentioned fourth embodiment.

As the above mentioned forceps part 219 is at the center axis 0, for the forceps coming out of this forceps part 219, the illumination dispersion by the illuminating lights emitted from the light guide tip surfaces 218A and 218B can be made small, the observation becomes easy and the operation also becomes easy. There are such effects.

Figure 16:
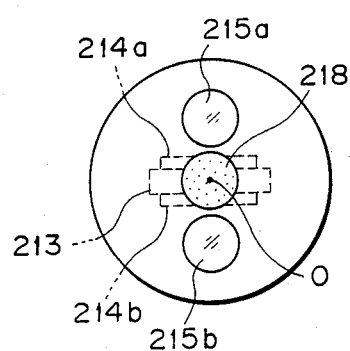
FIG. 16 is an elevation of the tip part of the insertable part in the sixth embodiment of the present invention.

FIG. 16 shows the sixth embodiment of the present invention.

This sixth embodiment is that, in the above mentioned fourth embodiment, the tip surface of the light guide 218 is arranged in the position of the center axis 0.

Thus, the outside diameter of the insertable part 202 can be made fine, the light amounts entering the two objective lenses 215a and 215b are not different and the object can be equally illuminated. By the way, in this embodiment, no forceps is provided.

Figure 17:
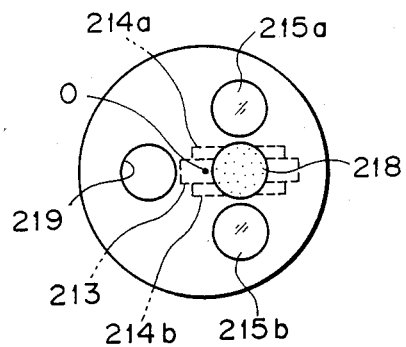
FIG. 17 is an elevation of the tip part of the insertable part in the seventh embodiment of the present invention.

FIG. 17 shows the seventh embodiment.

This seventh embodiment is that the imaging means contained within the tip part of the above mentioned sixth embodiment is made eccentric in the horizontal direction and the forceps part 219 is arranged on the side of this imaging means. The others are the same as in the above mentioned sixth embodiment.

Figure 18:
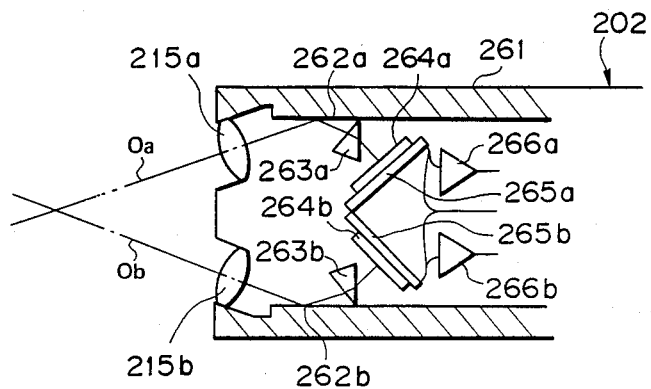
FIGS. 18 and 19 relate to the eighth embodiment of the present invention.
Figure 19:
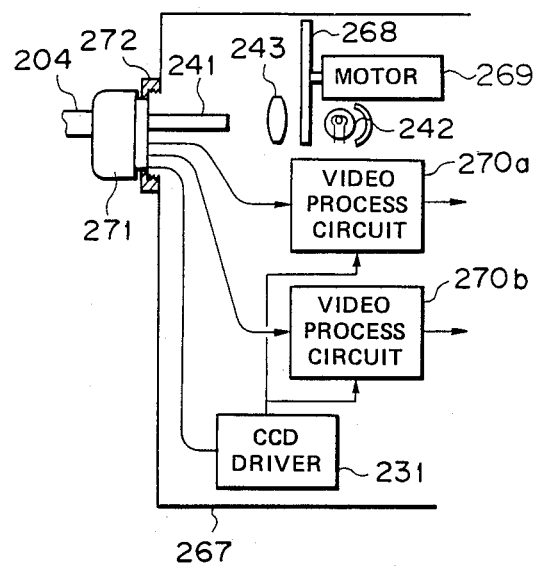

FIGS. 18 and 19 show the eighth embodiment of the present invention.

This eighth embodiment is that mirrors 262a and 262b arranged on the mirror surfaces in parallel with the axial direction of the insertable part 202 are provided instead of the mirrors 216a and 216b in the fourth embodiment shown in FIG. 10, the light path is changed by prisms 263a and 263b and CCD 264a and 264b are arranged on the imaging surfaces so as to intersect at right angles with the optical axis changed by these prisms 263a and 263b. That is to say, the above mentioned CCD 264a and 264b are arranged on the imaging surfaces respectively as inclined by a predetermined angle with the lengthwise direction of the insertable part 202.

The above mentioned CCD 264a and 264b are integrally fitted to connected packages 265a and 265b. The output signals of the CCD 264a and 264b are amplified by preamplifiers 266a and 266b of low noise exponents contained within the tip part 261 and are then transmitted to the video processor 267 side partly shown in FIG. 19 through transmitting cables.

In this embodiment, a frame sequential type color imaging system is used. That is to say, the light guide connector 241 is illuminated frame-sequentially with illuminating lights of R, G and B transmitted through a rotary filter 269 rotated by a motor 268. The signals imaged under these illuminating lights of R, G and B are input into frame sequential type video process circuits 270a and 270b through the pre-amplifiers 266a and 266b. Frame memories are provided within the respective video process circuits 270a and 270b. The signals read out of the respective frame memories are input into the picture image adjuster 235. The formation after this picture image adjuster 235 is the same as in the above mentioned fourth embodiment.

By the way, in this embodiment, the connector 271 fitted to the universal cord 204 is removably connected by screwing a connecting ring 272 to the male screw of the connector receptacle.

The operation and effect of this embodiment are substantially the same as in the above mentioned fourth embodiment but there is a possibility of making the outside diameter of the tip part 261 small by arranging the mirror surfaces of the mirrors 262a and 262b in parallel with the axial direction of the insertable part.

Figure 20:
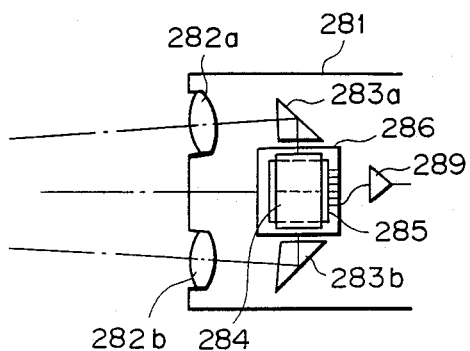
FIGS. 20 and 21 relate to the ninth embodiment of the present invention.
Figure 21:
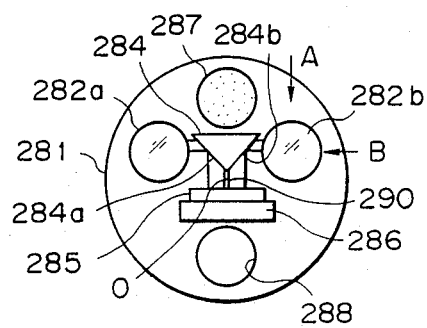

FIGS. 20 and 21 show the ninth embodiment of the present invention.

In this embodiment, two objective lenses 282a and 282b are arranged to be eccentric, for example, to the upper side from the center axis 0 as shown in FIG. 21 and all reflecting prisms 283a and 283b are arranged as shown in FIG. 20 in the rear positions on the optical axes of the respective objective lenses 282a and 282b. In FIG. 21, the respective prisms 283a and 283b are equal in the height positions (of the centers) to the respective objective lenses 282a and 282b but are somewhat different in the positions in the horizontal direction. That is to say, the prism 283a is somewhat diaplaced to the left from the objective lens 282 and the prism 283b is somewhat displaced to the right side from the objective lens 282b (not shown in FIG. 22).

The lights reflected by the respective prisms 283a and 283b are reflected by the respective slopes 284a and 284b of the prism 284 as shown in FIG. 21 and are made to form images on the imaging surface of the CCD 285 fitted to the package 286.

In this embodiment, the image formed on the above mentioned CCD 285 divides the imaging surface into two parts (into two parts in the horizontal direction in FIG. 21). The objective lenses 282a and 282b used in this embodiment have a cylindrical lens function or use combined non-spherical lenses. For example, the objective lens 282b in FIG. 21 is different in the curvatures in the horizontal direction and height direction. For example, the curvature (shape) as seen in the direction indicated by the arrow B is made larger than the curvature (shape) as seen in the direction indicated by the arrow A. The image formed on the CCD 285 is formed as compressed by about twice in the horizontal direction in FIG. 21.

By the way, in FIG. 21, a light guide 287 is arranged, for example, on the upper side of the prism 284 and a forceps part 288 is arranged on the lower side of the package 286. A light intercepting plate 290 is arranged on the lower side of the prism 284 so that the right and left lights may not interfere with each other.

The output of the above mentioned CCD 285 is amplified by a pre-amplifier 289 and is then input into the video processor side through a transmitting cable. In this video processor, in the direction in which the output is compressed by an extending circuit not illustrated, the output is extended by its compression ratio. This extension is made by reading out the signal data, for example, from the memory with $\frac{1}{2}$ the clock frequency and then the output is input into the picture image adjuster side.

In this embodiment, the same as in the first embodiment, as only one CCD 285 is used, the tip part 281 can be made small.

Figure 22:
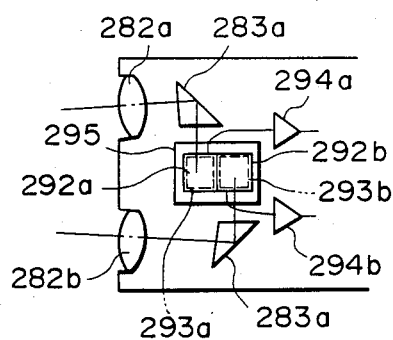
FIG. 22 is an explanatory view showing the tip part of the insertable part in the tenth embodiment of the present invention.

FIG. 22 shows the tenth embodiment of the present invention.

This embodiment is that, in the embodiment shown in FIG. 20, the positions of prisms 283a and 283b are displaced forward and rearward, are reflected respectively by the mirrors 292a and 292b and are made to form respective images on the CCD 293a and 293b arranged adjacently on the package 295 to which the plate surface becomes parallel in the axial direction of the insertable part (in FIG. 22, the plate surface of the package 295 and the imaging surfaces of the CCD 293a and 293b are parallel with the paper surface). By the way, for example, one mirror 292a is made on the mirror surface somewhat concave lens-like and can form an image on the CCD 293a even for a somewhat shorter light path length than of the other image forming optical system. The output signals of the respective CCD 293a and 293b are transmitted to the video processor side through pre-amplifiers 294a and 294b. In this case, such video processor as in shown in FIG. 11 or 19 can be used.

Now, in the fourth embodiment, the picture image is processed by displaying it with a stereo-picture image by the stereo-picture image synthesizing circuit 236. As in the second embodiment, two picture images are alternately displayed on the same displaying picture surface and the observer may control the opening and closing of the right and left shutters as synchronized with the picture images displayed alternately in the above by using spectacles provided with an electric shutter.

In the video processor 209 shown in the above mentioned FIG. 11, the memories 234a and 234b are provided after the video process circuits 233a and 233b but the outputs of the pre-amplifier 232a and 232b may be A/D-converted and may be memorized in the memories 234a and 234b.

By the way, an embodiment made by partly combined the above described respective embodiments also belong to the present invention.

In case the image is inverted by the mirror or the like, by changing the address in the case of reading out of the memory, at can be made a right image.

Thus, according to the fourth to tenth embodiments, an imaging means including a stereo-viewing solid state imaging device is compactly contained within the tip part of the insertable part and therefore a stereo-picture image can be obtained without making the tip part too thick or long.

By the way, the present invention is not limited to the above mentioned respective embodiments. For example, the stereo-picture image forming means is not limited to those shown in the above mentioned embodiments. For example, a lenticular lens may be used.

By the way, the present invention is not limited to a stereo-viewable electronic endoscope, object images in a plurality of places may be formed in a plurality of image forming regions of an imaging means, a plurality of places may be simultaneously observed and filters transmitting wavelength regions different from each other may be provided so that images of different wavelength regions of the same object may be simultaneously observed.

The present invention can be applied also to the case of measuring the height of the measuring position or the distance between the respective positions from a plurality of picture images having a parallax or displaying a quasi-stereo-image by a contour line or the like.

In this invention, it is apparent that working modes different in a wide range can be formed on the basis of this invention without deviating from the spirit and scope of the invention. This invention is not restricted by its specific working mode except being limited by the appended claims.

What is claimed is:

1. An electronic endoscope apparatus comprising:
   an elongate insertable part;
   two image forming optical systems provided in the tip part of said insertable part; and
   an imaging means provided in the tip part of said insertable part, having two imaging regions in which object images are formed by said two image forming optical systems and made integral.

2. An electronic endoscope apparatus according to claim 1 wherein said imaging means has one solid state imaging device having two imaging regions.

3. An electronic endoscope apparatus according to claim 1 further comprising an illuminating means illuminating an object to be imaged.

4. An electronic endoscope apparatus according to claim 1 further comprising a video signal processing means processing the output signal of said imaging means so as to be a video signal.

5. An electronic endoscope apparatus according to claim 4 wherein said video signal processing means has a visual field coverting means converting the visual fields of the images imaged in said two imaging regions.

6. An electronic endoscope apparatus according to claim 1 wherein said two image forming optical systems are arranged in two stereo-viewable positions.

7. An electronic endoscope apparatus according to claim 6 further comprising a video signal processing means processing the output signal of said imaging means so as to be a video signal and a stereo-image forming means forming a stereo-image of an object by using a video signal produced by said video signal processing means.

8. An electronic endoscope apparatus according to claim 7 wherein said stereo-image forming means has a monitor inputting a video signal from said video signal processing means and displaying on the right and left respective images imaged in said two imaging regions and a limiting means making obserable only one different from each other of the two images displayed on the right and left of said monitor respectively for the right and left eyes.

9. An electronic endoscope apparatus according to claim 8 wherein said limiting means comprises a polarizing plate provided on the front surface of said monitor and having a right side part and left side part passing only the lights in the polarizing directions different from each other and polarizing spectacles having a right part passing only the light in the same polarizing direction as of the right side part of said polarizing plate corresponding to the right eye and a left pat passing only the light in the same polarizing direction as of the left side part of said polarizing plate corresponding to the left eye.

10. An electronic endoscope apparatus according to claim 8 wherein said limiting means has a hood covering the displaying surface of said monitor, a partition plate provided within said hood and separating the displaying surface of said monitor to the right and left and two observing window parts provided on the right and left with said partition plate between them in said hood.

11. An electronic endoscope apparatus according to claim 7 wherein said stereo-image forming means has a signal processing means alternately outputting one of the video signals of the respective images imaged in said two imaging regions, a monitor inputting the video signals from said signal processing means and alternately displaying one of the respective images imaged in said two imaging regions and a pair of shutters alternately intercepting the light as synchronized with the switching of the image displayed in said monitor corresponding to the respective right and left eyes.

12. An electronic endoscope apparatus according to claim 11 wherein said signal processing means has a first memory memorizing two images imaged in said two imaging regions, second and third memories respectively memorizing the respective images memorized in said first memory and a memory controlling means alternately reading the images out of said second memory and third memory and delivering them to said monitor.

13. An electronic endoscope apparatus according to claim 11 wherein said signal processing means outputs a video signal so that the image of one side may be displayed in said monitor for 1/120 second every 1/60 second.

14. An electronic endoscope apparatus according to claim 1 wherein said imaging means has two solid state imaging devices made integral.

15. An electronic endoscope apparatus according to claim 14 wherein said two image forming optical systems are arranged as opposed to the center axis of said insertable part.

16. An electronic endoscope apparatus according to claim 14 further comprising an object illuminating means having two illuminating windows arranged on the straight line intersecting the straight line connecting the observing windows of said two image forming optical systems in the tip part of said insertable part.

17. An electronic endoscope apparatus according to claim 14 further comprising a treating tool channel provided within said insertable part and having a tip opening arranged in a position including the center axis of said insertable part.

18. An electronic endoscope apparatus according to claim 14 further comprising an object illuminating means having an illuminating window arranged between the observing windows of said two image forming optical systems in the tip part of said insertable part.

19. An electronic endoscope apparatus according to claim 14 wherein said two image forming optical systems are arranged so that the optical axes may intersect each other.

20. An electronic endoscope apparatus according to claim 14 further comprising a video signal processing means for processing the output signal of said imaging means so as to be a video signal having two process circuits whereby the video signal from said two solid state imaging devices is made a television signal, two memories respectively memorizing the output signals of said two process circuits and a picture image correcting circuit correcting the output signals of said two memories so that the sizes and position of the respective picture images may be the same.

21. An electronic endoscope apparatus according to claim 14 wherein said two solid state imaging devices are arranged with the respective imaging surfaces inclined by a predetermined angle with the center axis direction of said insertable part.

22. An electronic endoscope apparatus according to claim 14 wherein said two solid state imaging devices are fitted adjacently to one surface of a package.

23. An electronic endoscope apparatus according to claim 14 wherein said two solid state imaging devices have the same number of pixels.

24. An electronic endoscope apparatus according to claim 23 wherein the driving frequency driving said two solid state imaging devices is the same frequency.

25. An electronic endoscope apparatus according to claim 14 wherein said two solid state imaging devices are fitted to both surfaces of one package.

26. An electronic endoscope apparatus according to claim 25 wherein said two solid state imaging devices and package are arranged substantially parallelly with the axial direction of the insertable part substantially in the center axis position of the insertable part.

27. An electronic endoscope apparatus comprising:
an endoscope provided with an elongate insertable part, two image forming optical systems provided in the tip part of said insertable part and an integrated imaging means provided in the tip part of said insertable part and having two imaging regions in which object images are formed by said two image forming optical systems; and
a signal processing apparatus to which said endoscope is removably connected and which processes the output signal of said imaging means so as to be a video signal.

28. An electronic endoscope apparatus according to claim 27 wherein said imaging means has two solid state imaging devices made integral and said endoscope further has an adjusting means unifying the sizes of the video signals from said two solid state imaging devices.

29. An electronic endoscope apparatus according to claim 28 wherein said adjusting means is provided in a connector part connected to said signal processing apparatus.

30. An electronic endoscope apparatus comprising:
a elongate insertable part;
a plurality of image forming optical systems provided in the tip part of said insertable part; and
an integrated imaging means provided in the tip part of said insertable part and having a plurality of imaging regions in which object images are formed by said plurality of image forming optical systems.

* * * * *